United States Patent [19]

Yokoyama et al.

[11] Patent Number: 4,535,085
[45] Date of Patent: Aug. 13, 1985

[54] PERFLUOROTRICYCLIC AMINES AS OXYGEN CARRIERS

[75] Inventors: Kazumasa Yokoyama, Toyonaka; Chikara Fukaya, Osaka; Yoshio Tsuda, Takarazuka; Taizo Ono, Osaka; Yoshio Arakawa; Yoshihisa Inoue, both of Suita; Youichiro Naito, Hirakata; Tadakazu Suyama, Kyoto, all of Japan

[73] Assignee: The Green Cross Corporation, Osaka, Japan

[21] Appl. No.: 480,131

[22] Filed: Mar. 29, 1983

[51] Int. Cl.³ .................. A61K 31/445; A61K 31/40; C07D 221/16; C07D 221/22
[52] U.S. Cl. .................................... 514/290; 514/295; 514/411; 546/79; 546/93; 546/97; 546/101; 546/111; 548/427; 548/434
[58] Field of Search .................. 548/427, 434; 546/79, 546/93, 97, 101, 111; 424/267, 274

[56] References Cited

U.S. PATENT DOCUMENTS 4,105,798   8/1978   Moore et al. .................. 424/352

OTHER PUBLICATIONS

*Chemical Abstracts,* 85:99179e (1976) [Moore, R., et al., Ger. Offen. 2,555,408, 6/10/76].

*Chemical Abstracts,* 90:84603t (1979) [Wechsberg, M., Ger. Offen. 2,725,211, 12/14/78].

*Primary Examiner*—Richard A. Schwartz
*Attorney, Agent, or Firm*—Cushman, Darby & Cushman

[57] ABSTRACT

A perfluorotricyclic amine compound which is usable as an oxygen carrier in an artificial blood, represented by the general formula

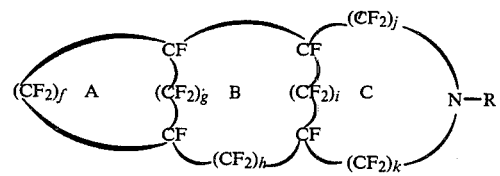

wherein R denotes a perfluoroalkyl group having 1–4 carbon atoms; the ring A denotes a five- or six-membered ring, the ring B denotes a five-, six- or seven-membered ring, the ring C denotes a five- or six-membered ring any one of the rings A, B and C optionary being substituted by one or more lower perfluoroalkyl group in addition to the above-mentioned substituent R; and further f, g, h, i, j and k denote integers appropriately selected to construct the above-mentioned size of rings A, B, and C; is prepared by reacting the corresponding perhydrotricyclic amine with fluorine.

4 Claims, No Drawings

PERFLUOROTRICYCLIC AMINES AS OXYGEN CARRIERS

This invention relates to a novel perfluorotricyclic amine compound useful as an oxygen carrier in artificial blood or in an infusion fluid.

More particularly, it relates to perfluorotricyclic amine compounds represented by the general formula

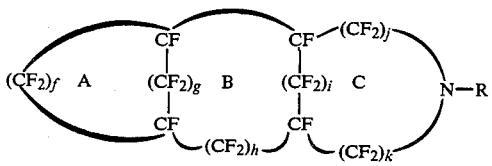

(I)

wherein R denotes a perfluoroalkyl group having from 1 to 4 carbon atoms, the ring A denotes a five- or six-membered ring, the ring B denotes a five-, six- or seven-membered ring, the ring C denotes a five- or six-membered ring, and f, g, h, i, j and k denote integers appropriately selected to construct the above-mentioned size of rings A, B and C. In that case, the compound may be substituted by one or more lower perfluoroalkyl group(s) in addition to the above-mentioned substituent R.

Regarding the general formula (I), as mentioned above, f, g, h, i, j and k are integers appropriately selected to construct a five- or six-membered ring A, a five-, six- or seven-membered ring B and a five- or six-membered ring C, respectively. Individually, each of the integers is appropriately selected, for example, from: 1, 2, 3 and 4 for f; 0, 1 and 2 for g; 0 and 1 for h; and 0, 1, 2 and 3 for each of i, j and k.

In the general formula (I), the lower perfluoroalkyl group denoted by R may be either of straight chain or of branched chain. Examples thereof include those having 1 to 4, preferably 1 to 2, carbon atoms, such as perfluoromethyl group, perfluoroethyl group, perfluoro-n-propyl group, perfluoroisopropyl group, perfluoro-n-butyl group, perfluoroisobutyl group, perfluoro-sec-butyl group and perfluoro-tert-butyl group.

Rings A, B and C, especially rings A and C may be substituted at any position thereof by one or more than one, preferably one or two, lower perfluoroalkyl group(s) in addition to the above-mentioned substituent denoted by R. Examples of the lower perfluoroalkyl groups suitable as such substituents are similar to those which are described above referring to R. Perfluoromethyl group is especially preferred. In case where two or more of substituents are present, they may be different from each other.

The total number of carbon atoms present in the compound of formula (I) is generally from 8 to 12, preferably 10 or 11.

As an embodiment of the compound of formula (I), mention may be made of a compound represented by the general formula

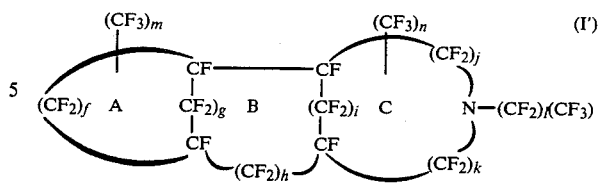

(I')

wherein rings A, B and C are as defined above; $f+g+h+i+j+k+l+m+n=5$ or 6; f denotes 1, 2, 3 or 4; g denotes 0, 1 or 2; h, l, m and n denote each 0 or 1; and i, j and k denote each 0, 1, 2 or 3.

The compound of formula (I) can be prepared by fluorinating a perhydro-compound corresponding to the compound of formula (I). The methods of fluorination include, for example, a direct fluorination, a fluorination by use of cobalt trifluoride, and an electro chemical fluorination.

The preparation of the compound of formula (I) of this invention is preferably performed by the electrochemical fluorination method. This is performed, for example, by mixing anhydrous hydrogen fluoride and a perhydro-compound used as the starting compound in an electrolytic cell and subjecting the resulting solution to electrolysis. The voltage, the current density at the anode, and the temperature of electrolytic solution are normally 3–9 V, 0.2–3.0 A/dm$^2$ and 4°–10° C., respectively.

The compound of formula (I) thus formed was drained from the bottom of the cell, being insoluble in anhydrous hydrogen fluoride.

The isolation and purification of the compound from the drained product are carried out, for example, by adding a mixture of equal volumes of an aqueous alkaline solution and an amine compound to the drained product, refluxing, then separating the lowermost layer containing the desired compound of formula (I) (the partially fluorinated compounds decomposed in this process), washing the former layer with an aqueous acetone solution containing a suitable amount of potassium iodide to remove perfluoroalkyl nitrogen fluorides, and by subsequent fractional distillation to obtain the fraction of the desired compound of formula (I).

Since the compound of the formula (I) of this invention can dissolve a large amount of oxygen, is chemically and biologically inert, and can be excreted rapidly from the body, it can form, for example, an aqueous emulsion containing 5 to 50, preferably 10–40, %(W/V) of the compound of formula (I) to be used as an oxygen carrier in an artificial blood or in an infusion liquid for men and other mammals such as dogs, cats, cattle, mice, rats and guinea pigs.

The symbol "%(W/V)" referred to herein mean the amount of the material by weight (gram) based on 100 ml of the resulting emulsion.

In the preparation of the emulsion mentioned above, there used, as an emulsifier, a nonionic surfactant or phospholipids in an added amount of 1 to 5% (W/V).

As the medium for the emulsion, a physiologically acceptable aqueous solution is employed. If necessary, there may be added thereto such materials as inorganic salts to provide the desired isotonicity, and such plasma expanders as HES or dextran to regulate the osmotic pressure of the emulsion.

The emulsion can be prepared by mixing the above-mentioned ingredients and homogenizing the mixture by means of, for example, a high-pressure jet type homogenizer until the particle diameters become 0.05 to 0.3 μm, preferably less than 0.2 μm.

The perhydro-compounds (starting compounds) corresponding to the compounds of formula (I) are substantially known already.

EXAMPLE

The equipment employed in the fluorination was a Monel reaction cell, through which coolant could be circulated for temperature control. Power was supplied to the cell pack by a 0–50 amp, 0–50 V.DC power supply. The cell pack consisted of 13 nickel plates (more than 99.6% purity) separated with Teflon spacers, and arranged alternately so that the seven odd numbered plates were cathodes and the six even numbered plates were anodes.

The spacing between plates was 1.7–2.0 mm. The cell was equipped with a copper condenser, through which coolant was circulated by a refrigeration unit. The progress of an electrolysis was monitered by a voltage-current recorder. In the electrolytic cell, was placed 1.2 liter of hydrogen fluoride, and trace amounts of impurities present in the system (moisture or sulfuric acid) were removed by preliminary electrolysis. Then, 0.675 mol (102 g) of 4-methyl-4-azatricyclo[5,2,1,0$^{2,6}$]decane was introduced into the cell, and the electrolysis was continued, while introducing nitrogen gas from the bottom of the cell at a rate of 100 ml/min., under the conditions of anode current density of 0.4–2.0 A/dm$^2$, voltage of 5–7 V and solution temperature of 7°–12° C., until the ampere-hours amounted to 730. Fresh anhydrous hydrogen fluoride (300 ml) was added every 24 hours during the electrolysis. No attempt was made to collect volatile products formed by a bond breaking reaction. After completion of the electrolysis, fluorocarbons in the lower layer in the cell was drained through the bottom of the cell, weighed 260 g (57% yield).

To the fluorocarbons thus separated, were added equal volumes of 70% aqueous potassium hydroxide solution and diisobutylamine, and the resulting mixture was refluxed for about five days. The reaction mixture was then cooled in an ice bath. The perfluoro-compounds sedimented in the lowermost layer were separated in a separatory funnel, washed successively with water, concentrated sulfuric acid, saturated aqueous sodium hydrogen carbonate solution and 90% aqueous acetone solution containing 3% of potassium iodide, and finally several times with water to yield 162.0 g of perfluoro-compounds containing no protons. This was distilled on a fractional distillation apparatus equipped with a spinning band column to afford 39.2 g (8.6% yield) of the desired product boiling at 143°–152° C. This product was purified, then analyzed by infrared absorption spectrometry, $^{19}$F-nuclear magnetic resonance spectrometory and mass spectrometory, and was confirmed to be the objective compound, perfluoro-4-methyl-4-azatricyclo[5,2,1,0$^{2,6}$]decane.

A series of other perfluorotricyclic amine compounds were synthesized and purified in the same manner as that described above and each product was confirmed to be the objective compound upon analysis by infrared absorption spectrometory, $^{19}$F-nuclear magnetic resonance spectrometory and mass spectrometory.

The structural formula and the boiling point of each of the objective compounds is shown in the Table. The symbol "F-" in the structural formula indicates that the compound is perfluorinated. For example, the formula

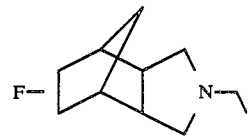

indicates in its exact meaning the formula

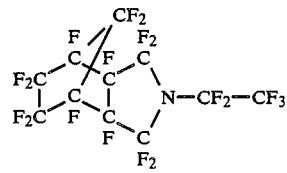

TABLE

| No. | Starting material Compound | Objective compound | Boiling point (°C.) |
| --- | --- | --- | --- |
| 1 | 4-Methyl-4-azatricyclo[5,2,1,0$^{2,6}$]-decane | | 143–152 |
| 2 | 4-Ethyl-4-azatricyclo[5,2,1,0$^{2,6}$]-decane | | 158–166 |
| 3 | 3,4-Dimethyl-4-azatricyclo-[5,2,1,0$^{2,6}$]decane | | 157–166 |

TABLE-continued

| No. | Starting material Compound | Objective compound | Boiling point (°C.) |
|---|---|---|---|
| 4 | 2,4-Dimethyl-4-azatricyclo-[5,2,1,0$^{2,6}$]decane | (structure) | 156–165 |
| 5 | 1,4-Dimethyl-4-azatricyclo-[5,2,1,0$^{2,6}$]decane | (structure) | 156–165 |
| 6 | 4,8-Dimethyl-4-azatricyclo-[5,2,1,0$^{2,6}$]decane | (structure) | 157–166 |
| 7 | 4,10-Dimethyl-4-azatricyclo-[5,2,1,0$^{2,6}$]decane | (structure) | 156–166 |
| 8 | 3-Methyl-3-azatricyclo-[5,2,1,0$^{2,6}$]decane | (structure) | 143–153 |
| 9 | 3-Ethyl-3-azatricyclo-[5,2,1,0$^{2,6}$]decane | (structure) | 157–166 |
| 10 | 1,3-Dimethyl-3-azatricyclo-[5,2,1,0$^{2,6}$]decane | (structure) | 156–165 |
| 11 | 2,3-Dimethyl-3-azatricyclo-[5,2,1,0$^{2,6}$]decane | (structure) | 155–165 |
| 12 | 3,4-Dimethyl-3-azatricyclo-[5,2,1,0$^{2,6}$]decane | (structure) | 155–166 |
| 13 | 3,5-Dimethyl-3-azatricyclo-[5,2,1,0$^{2,6}$]decane | (structure) | 156–166 |

TABLE-continued

| No. | Starting material Compound | Objective compound | Boiling point (°C.) |
|---|---|---|---|
| 14 | 3,6-Dimethyl-3-azatricyclo-[5,2,1,0$^{2,6}$]decane | | 155–165 |
| 15 | 3,7-Dimethyl-3-azatricyclo-[5,2,1,0$^{2,6}$]decane | | 154–165 |
| 16 | 3,8-Dimethyl-3-azatricyclo-[5,2,1,0$^{2,6}$]decane | | 156–166 |
| 17 | 3,9-Dimethyl-3-azatricyclo-[5,2,1,0$^{2,6}$]decane | | 156–166 |
| 18 | 3,10-Dimethyl-3-azatricyclo-[5,2,1,0$^{2,6}$]decane | | 155–166 |
| 19 | 4-Methyl-4-azatricyclo-[6,2,1,0$^{2,7}$]decane | | 156–166 |
| 20 | 3-Methyl-3-azatricyclo-[6,2,1,0$^{2,7}$]undecane | | 156–166 |
| 21 | 4-Methyl-4-azatricyclo-[5,2,1,1$^{2,6}$]undecane | | 155–166 |
| 22 | 3-Methyl-3-azatricyclo-[5,2,1,1$^{2,6}$]undecane | | 155–166 |
| 23 | 4-Methyl-4-azatricyclo-[5,2,2,0$^{2,6}$]undecane | | 155–165 |

TABLE-continued

| No. | Starting material Compound | Objective compound | Boiling point (°C.) |
|---|---|---|---|
| 24 | 3-Methyl-3-azatricyclo-[5,2,2,0$^{2,6}$]undecane | | 155–165 |
| 25 | 4-Methyl-4-azatricyclo-[5,3,1,0$^{2,6}$]undecane | | 155–165 |
| 26 | 3-Methyl-3-azatricyclo-[5,3,1,0$^{2,6}$]undecane | | 155–165 |
| 27 | 4-Methyl-4-azatricyclo-[6,2,1,0$^{2,6}$]undecane | | 156–166 |
| 28 | 3-Methyl-3-azatricyclo-[6,2,1,0$^{2,6}$]undecane | | 156–166 |
| 29 | 5-Methyl-5-azatricyclo-[6,2,1,0$^{2,6}$]undecane | | 156–166 |
| 30 | 4-Methyl-4-azatricyclo-[6,3,0,0$^{2,6}$]undecane | | 155–166 |
| 31 | 3-Methyl-3-azatricyclo-[6,3,0,0$^{2,6}$]undecane | | 155–166 |
| 32 | 5-Methyl-5-azatricyclo-[6,3,0,0$^{2,6}$]undecane | | 155–166 |
| 33 | 8-Methyl-8-azatricyclo-[5,3,1,0$^{2,6}$]undecane | | 155–165 |

TABLE-continued

| No. | Starting material Compound | Objective compound | Boiling point (°C.) |
|---|---|---|---|
| 34 | 9-Methyl-9-azatricyclo-[5,3,1,0$^{2,6}$]undecane | | 155–165 |
| 35 | 3-Methyl-3-azatricyclo-[4,2,1,1$^{2,5}$]decane | | 143–153 |
| 36 | 3-Ethyl-3-azatricyclo-[4,2,1,1$^{2,5}$]decane | | 157–167 |
| 37 | 1,3-Dimethyl-3-azatricyclo-[4,2,1,1$^{2,5}$]decane | | 156–166 |
| 38 | 2,3-Dimethyl-3-azatricyclo-[4,2,1,1$^{2,5}$]decane | | 156–166 |
| 39 | 3,4-Dimethyl-3-azatricyclo-[4,2,1,1$^{2,5}$]decane | | 156–166 |
| 40 | 3,5-Dimethyl-3-azatricyclo-[4,2,1,1$^{2,5}$]decane | | 155–165 |
| 41 | 3,6-Dimethyl-3-azatricyclo-[4,2,1,1$^{2,5}$]decane | | 155–165 |
| 42 | 3,7-Dimethyl-3-azatricyclo-[4,2,1,1$^{2,5}$]decane | | 155–166 |
| 43 | 3,8-Dimethyl-3-azatricyclo-[4,2,1,1$^{2,5}$]decane | | 156–166 |
| 44 | 3,9-Dimethyl-3-azatricyclo-[4,2,1,1$^{2,5}$]decane | | 156–166 |

TABLE-continued

| No. | Starting material Compound | Objective compound | Boiling point (°C.) |
|---|---|---|---|
| 55 | 6,8-Dimethyl-8-azatricyclo-[5,2,1,0$^{2,6}$]decane | | 156–166 |
| 56 | 7,8-Dimethyl-8-azatricyclo-[5,2,1,0$^{2,6}$]decane | | 156–166 |
| 57 | 8,9-Dimethyl-8-azatricyclo-[5,2,1,0$^{2,6}$]decane | | 143–153 |
| 58 | 8,10-Dimethyl-8-azatricyclo-[5,2,1,0$^{2,6}$]decane | | 157–168 |
| 59 | 9-Methyl-9-azatricyclo-[6,2,1,0$^{2,7}$]undecane | | 156–167 |
| 60 | 9-Methyl-9-azatricyclo[6,2,1,0$^{2,6}$]-undecane | | 156–167 |
| 61 | 9-Methyl-9-azatricyclo-[6,2,1,0$^{3,7}$]undecane | | 156–167 |
| 62 | 3-Methyl-3-azatricyclo-[4,3,1,1$^{2,5}$]undecane | | 157–168 |
| 63 | 10-Methyl-10-azatricyclo-[5,2,2,0$^{2,6}$]undecane | | 156–157 |
| 64 | 11-Methyl-11-azatricyclo-mx,1 [5,3,1,0$^{2,6}$]undecane | | 156–165 |

TABLE-continued

| No. | Starting material Compound | Objective compound | Boiling point (°C.) |
|---|---|---|---|
| 45 | 3,10-Dimethyl-3-azatricyclo-[4,2,1,1$^{2,5}$]decane | | 156–166 |
| 46 | 3-Methyl-3-azatricyclo-[5,2,1,1$^{2,5}$]undecane | | 156–167 |
| 47 | 4-Methyl-4-azatricyclo-[5,2,1,1$^{2,6}$]undecane | | 156–167 |
| 48 | 8-Methyl-8-azatricyclo-[5,2,1,0$^{2,6}$]decane | | 143–153 |
| 49 | 8-Ethyl-8-azatricyclo-[5,2,1,0$^{2,6}$]decane | | 156–167 |
| 50 | 1,8-Dimethyl-8-azatricyclo-[5,2,1,0$^{2,6}$]decane | | 155–167 |
| 51 | 2,8-Dimethyl-8-azatricyclo-[5,2,1,0$^{2,6}$]decane | | 155–167 |
| 52 | 3,8-Dimethyl-8-azatricyclo-[5,2,1,0$^{2,6}$]decane | | 156–166 |
| 53 | 4,8-Dimethyl-8-azatricyclo-[5,2,1,0$^{2,6}$]decane | | 157–167 |
| 54 | 5,8-Dimethyl-8-azatricyclo-[5,2,1,0$^{2,6}$]decane | | 157–167 |

TABLE-continued

| No. | Starting material Compound | Objective compound | Boiling point (°C.) |
|---|---|---|---|
| 65 | 10-Methyl-10-azatricyclo-[5,2,1,0²,⁶]decane | | 143–152 |
| 66 | 10-Ethyl-10-azatricyclo-[5,2,1,0²,⁶]decane | | 156–165 |
| 67 | 1,10-Dimethyl-10-azatricyclo-[5,2,1,0²,⁶]decane | | 155–164 |
| 68 | 2,10-Dimethyl-10-azatricyclo-[5,2,1,0²,⁶]decane | | 155–165 |
| 69 | 3,10-Dimethyl-10-azatricyclo-[5,2,1,0²,⁶]decane | | 156–166 |
| 70 | 4,10-Dimethyl-10-azatricyclo-[5,2,1,0²,⁶]decane | | 156–166 |
| 71 | 8,10-Dimethyl-10-azatricyclo-[5,2,1,0²,⁶]decane | | 156–166 |
| 72 | 11-Methyl-11-azatricyclo-[6,2,1,0²,⁷]undecane | | 155–165 |
| 73 | 9-Methyl-9-azatricyclo-[4,2,1,1²,⁵]decane | | 142–153 |
| 74 | 9-Ethyl-9-azatricyclo-[4,2,1,1²,⁵]decane | | 155–165 |
| 75 | 1,9-Dimethyl-9-azatricyclo-[4,2,1,1²,⁵]decane | | 154–165 |
| 76 | 2,9-Dimethyl-9-azatricyclo-[4,2,1,1²,⁵]decane | | 154–165 |

TABLE-continued

| No. | Starting material Compound | Objective compound | Boiling point (°C.) |
|---|---|---|---|
| 77 | 3,9-Dimethyl-9-azatricyclo-[4,2,1,1$^{2,5}$]decane | | 156–166 |
| 78 | 7,9-Dimethyl-9-azatricyclo-[4,2,1,1$^{2,5}$]decane | | 156–165 |
| 79 | 9,10-Dimethyl-9-azatricyclo-[4,2,1,1$^{2,5}$]decane | | 156–166 |
| 80 | 10-Methyl-10-azatricyclo-[5,2,1,1$^{2,6}$]undecane | | 156–166 |
| 81 | 11-Methyl-11-azatricyclo-[6,2,1,0$^{2,6}$]undecane | | 155–166 |
| 82 | 10-Methyl-10-azatricyclo-[5,2,1,1$^{2,5}$]undecane | | 156–166 |

What is claimed is:

1. A perfluorotricyclic amine compound represented by the formula

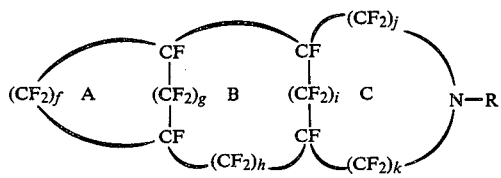

wherein R denotes a perfluoroalkyl group having 1 to 4 carbon atoms; the ring A denotes a five- or six-membered ring, the ring B denotes a five-, six- or seven-membered ring, the ring C denotes a five- or six-membered ring any one of the rings A, B and C optionally being substituted by one or more lower perfluoroalkyl groups in addition to the above-mentioned substituent R: and further f, g, h, i, j and k denote integers appropriately selected to construct the above-mentioned size of rings A, B and C.

2. A composition for use as a blood substitute or an infusion fluid which composition is an aqueous emulsion of a perfluorotricyclic amine as defined in claim 1.

3. A composition according to claim 2, which contains from 5 to 50% (w/v) of the perfluorotricyclic amine of claim 1 and, as emulsifier, a nonionic surfactant and/or phospholipid.

4. A composition according to claim 2, in which the particle size of the perfluorotricyclic amine is 0.05 to 0.3 μm.

* * * * *